United States Patent
Uehara et al.

(10) Patent No.: US 8,663,613 B2
(45) Date of Patent: *Mar. 4, 2014

(54) HAIR OR SKIN CONDITIONING COMPOSITIONS COMPRISING HYDROPHOBICALLY MODIFIED AMIDO SILICONE COPOLYOL

(71) Applicant: The Procter & Gamble Company, Cincinnati, OH (US)

(72) Inventors: Nobuaki Uehara, Kobe (JP); Satomi Asari, Kobe (JP); Natsumi Komure, Ashiya (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/849,281

(22) Filed: Mar. 22, 2013

(65) Prior Publication Data

US 2013/0236412 A1 Sep. 12, 2013

Related U.S. Application Data

(63) Continuation of application No. 11/362,640, filed on Feb. 27, 2006, now Pat. No. 8,420,065.

(60) Provisional application No. 60/656,589, filed on Feb. 25, 2005, provisional application No. 60/693,897, filed on Jun. 24, 2005.

(51) Int. Cl.
*A61Q 5/12* (2006.01)
*A61K 8/73* (2006.01)
*A61K 8/02* (2006.01)

(52) U.S. Cl.
USPC ............. 424/70.122; 424/70.27; 424/70.13; 510/122

(58) Field of Classification Search
None
See application file for complete search history.

(56) References Cited

U.S. PATENT DOCUMENTS

2004/0247550 A1 12/2004 Asari
2005/0175568 A1 8/2005 Asari

FOREIGN PATENT DOCUMENTS

WO 2004032887 4/2004

OTHER PUBLICATIONS

International Search Report, PCT/US2006/006004; Mailing Date Jun. 7, 2006; 10 pages.

*Primary Examiner* — David J Blanchard
*Assistant Examiner* — Lori K Mattison
(74) *Attorney, Agent, or Firm* — Linda M. Sivik

(57) ABSTRACT

Disclosed are hair or skin conditioning compositions comprising by weight: (a) from about 0.1% to about 10% of a thickening polymer system; (b) from about 0.1% to about 8.0% of a surfactant system selected from the group consisting of cationic surfactant, nonionic surfactant, and mixtures thereof; (c) from about 0.1% to about 10% of a hydrophobically modified amido silicone copolyol; and (d) an aqueous carrier; wherein the composition has a transmittance of 25% or more and/or wherein the composition has a viscosity of from about 1,000 cps to about 50,000 cps and Shear Thinning Index of 30 or more. The compositions are especially suitable for hair care products such as hair conditioning products for rinse-off/leave-on use.

20 Claims, No Drawings

HAIR OR SKIN CONDITIONING COMPOSITIONS COMPRISING HYDROPHOBICALLY MODIFIED AMIDO SILICONE COPOLYOL

This application is a continuation of U.S. application Ser. No. 11/362,640, filed on Feb. 27, 2006, now U.S. Pat. No. 8,420,065.

FIELD OF THE INVENTION

The present invention relates to hair or skin conditioning compositions comprising: (a) a thickening polymer system; (b) a surfactant system selected from the group consisting of cationic surfactant, nonionic surfactant, and mixtures thereof; (c) a hydrophobically modified amido silicone copolyol; and (d) an aqueous carrier; wherein the composition has a transmittance of 25% or more and/or wherein the composition has a viscosity of from about 1,000 cps to about 50,000 cps and Shear Thinning Index of 30 or more. The compositions are especially suitable for hair care products such as hair conditioning products for rinse-off/leave-on use.

BACKGROUND OF THE INVENTION

A variety of conditioning compositions such as hair conditioning compositions and skin conditioning compositions have been used for a variety of substrates such as hair and skin. A common method of providing conditioning benefits is through the use of conditioning agents such as cationic surfactants and polymers, high melting point fatty compounds, low melting point oils, silicone compounds, and mixtures thereof. Most of these conditioning agents are known to provide various conditioning benefits. For example, some cationic surfactants, when used together with some high melting point fatty compounds, are believed to form a gel matrix which has a suitable rheology for conditioning compositions and which is suitable for providing a variety of conditioning benefits, especially when used for hair care products, such as slippery feel, softness and reduced tangling on wet hair and softness and moisturized feel on the dry hair.

Most of the above conditioning agents are also known to make the composition opaque. Thus, there is a need for conditioning compositions having a clear product appearance i.e., transparent or translucent product appearance.

Additionally, there exists a need for achieving a suitable rheology for conditioning compositions by other methods than forming the above gel matrix, while maintaining the conditioning benefits of the gel matrix.

Furthermore, most of the above conditioning agents are also known to weigh down the hair when these conditioning agents are included in hair care compositions. For consumers who desire maintaining or increasing hair volume such as consumers having fine hair, weighing down the hair is not desirable. Thus, there is a need for hair conditioning compositions which do not weigh down the hair while providing conditioning benefits.

Based on the foregoing, there remains a need for conditioning compositions which provide a clear product appearance. There also remains a need for such conditioning compositions which provide a suitable rheology. There is also a need for such conditioning compositions which are suitable for providing further benefits such as sufficient conditioning benefits and/or not weighing down the hair, while providing a clear product appearance and/or a suitable rheology.

None of the existing art provides all of the advantages and benefits of the present invention.

SUMMARY OF THE INVENTION

The present invention is directed to hair or skin conditioning compositions comprising by weight:
(a) from about 0.1% to about 10% of a thickening polymer system;
(b) from about 0.1% to about 8.0% of a surfactant system selected from the group consisting of cationic surfactant, nonionic surfactant, and mixtures thereof;
(c) from about 0.1% to about 10% of a hydrophobically modified amido silicone copolyol; and
(d) an aqueous carrier;
wherein the composition has a transmittance of 25% or more, and/or wherein the composition has a viscosity of from about 1,000 cps to about 50,000 cps and Shear Thinning Index of 30 or more These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Compositions

The hair or skin conditioning composition of the present invention comprises by weight:
(a) from about 0.1% to about 10% of a thickening polymer system;
(b) from about 0.1% to about 8.0% of a surfactant system selected from the group consisting of cationic surfactant, nonionic surfactant, and mixtures thereof;
(c) from about 0.1% to about 10% of a hydrophobically modified amido silicone copolyol; and
(d) an aqueous carrier;
wherein the composition has a transmittance of 25% or more and/or wherein the composition has a viscosity of from about 1,000 cps to about 50,000 cps and Shear Thinning Index of 30 or more The conditioning compositions of the present invention have a clear product appearance with or without additional components such as perfumes and/or have a suitable rheology for conditioning compositions. Furthermore, the conditioning compositions of the present invention are suitable for providing conditioning benefits, especially softness and reduced tangling when used for hair care products such as hair conditioning products, and not weighing down the hair when used for hair care products such as hair conditioning products.

The composition of the present invention has a transmittance of 25% or more, thus, has a clear product appearance, i.e., translucent or transparent product appearance. Preferably, the composition of the present invention has a transmittance of about 35% or more, preferably 40% or more, more preferably about 50% or more, still more preferably about 60% or more. The transmittances are measured at 600 nm using UV-1601, which is a UV-visible spectrophotometer available from Shimadzu. In view of the desire for clear product appearance, it is preferred that the composition of the present invention has the above transmittance for at least one month, more preferably for at least three months, still more preferably for at least one year at 25° C., following preparation of the composition.

In view of clear product appearance, the compositions of the present invention are preferably substantially free of substantially insoluble oily compounds. In the present invention, the compositions being "substantially free" of substantially insoluble oily compound means that the composition includes 1.0% or less, preferably 0.5% or less, more preferably 0.1% or less, still more preferably 0% of substantially insoluble oily compounds. By "substantially insoluble" oily compound, what is meant is that: the oily compound is substantially insoluble in the compositions at the level used; and, when containing the oily compounds at the level used, the compositions has a transmittance of below about 25%, preferably below about 35%, more preferably below about 40%, still more preferably below about 50%, even more preferably below about 60% at 25° C. Such "substantially insoluble" oily compounds are typically those selected from hydrocarbons, fatty compounds, and mixtures thereof. Such hydrocarbons include, for example, poly α-olefin oils, paraffins, waxes, and mixtures thereof. Such fatty compounds include, for example, fatty alcohols such as cetyl alcohol and stearyl alcohol, fatty acids such as stearic acid, fatty alcohol derivatives and fatty acid derivatives such as esters and ethers thereof, and mixtures thereof.

In view of the desire for clear product appearance, especially in view of avoiding yellowing of the product appearance, it is preferred that the composition of the present invention is substantially free of a compound having primary amine group (—NH$_2$). In the present invention, the compositions being "substantially free" of a compound having primary amine group means that the composition includes 1.0% or less, preferably 0.5% or less, more preferably 0.1% or less, still more preferably 0% of such compounds. Preferably, the composition of the present invention has non-yellowed clear product appearance for at least one month, more preferably for at least three months, still more preferably for at least one year at 25° C., following preparation of the composition.

Preferably, the compositions of the present invention are substantially free of anionic compounds. Anionic compounds herein include anionic surfactants and anionic polymers. In the present invention, the compositions being "substantially free of anionic compounds" means that the compositions include 1% or less, preferably 0.5% or less, more preferably 0% of anionic compounds.

Thickening Polymer System

The compositions of the present invention comprise a thickening polymer system. The thickening polymers useful herein are those which can provide appropriate viscosity and rheology properties to the composition, so that the compositions of the present invention have: (i) a suitable viscosity of preferably from about 1,000 cps to about 50,000 cps, more preferably from about 5,000 cps to about 40,000 cps, still more preferably from about 10,000 cps to about 35,000 cps; and (ii) suitable rheology properties such that the compositions have a Shear Thinning Index (STI) of preferably about 30 or more, more preferably about 50 or more, and when the compositions are for rinse-off use, still more preferably about 70 or more. Preferably, the composition of the present invention has the above viscosity and STI for at least one month, more preferably for at least three months, still more preferably for at least one year at 25° C., following preparation of the composition. The viscosity herein can be suitably measured by Brookfield RVT at a shear rate of 2·s$^{-1}$ at 26.7° C. The Shear Thinning Index (STI) is calculated according to the following equation:

$$\text{Shear Thinning Index(STI)} = \text{a first viscosity/a second viscosity};$$

wherein the first viscosity is measured at a shear rate of 2·s$^{-1}$, and the second viscosity is measured at a shear rate of 950·s$^{-1}$, both at 26.7° C. by shear rate ramp flow measurement using AR 2000 available from TA Instruments.

The composition of the present invention comprises by weight of from about 0.1% to about 10%, preferably from about 0.25% to about 8%, more preferably from about 0.5% to about 5%, still more preferably from about 0.75% to about 4%, even more preferably from about 0.85% to about 3%, highly preferably from about 1.0% to about 2.5%, of total thickening polymers.

A variety of thickening polymers can be used in the compositions of the present invention. Thickening polymers useful herein include, for example, cellulose and its derivatives such as cellulose ethers, hydrophobically modified cellulose ethers, and quaternized celluloses; nonionic guar gums; cationic guar gums; crosslinked polymers such as nonionic crosslinked polymers and cationic crosslinked polymers; and acrylate polymers such as sodium polyacrylate, polyethylacrylate, and polyacrylamide. The thickening polymers useful herein may include the polymers disclosed below under the title "CATIONIC POLYMER". Among a variety of thickening polymers, preferred are nonionic guar gums. Preferably, the thickening polymer system is nonionic.

Nonionic Guar Polymer

In the composition, nonionic guar polymers are preferably used among a variety of thickening polymers.

The nonionic guar polymer useful herein has a molecular weight of preferably from about 500,000 AMU (Atomic Mass Unit) to about 4,000,000 AMU, more preferably from about 1,000,000 AMU to about 3,500,000 AMU, still more preferably from about 1,600,000 AMU to about 3,000,000 AMU, even more preferably from about 1,900,000 AMU to about 2,800,000 AMU. Commercially available nonionic guar polymers useful herein include, for example, that having a molecular weight of about 2,000,000 AMU and having a tradename Jaguar HP-105 available from Rhodia, and N-hance HP series such as 40 and 40S available from Aqualon.

Surfactant System

The compositions of the present invention comprise a surfactant system. The surfactant system is included in the compositions at a level by weight of from about 0.1% to about 8.0%, preferably from about 0.2% to about 5.0%, more preferably from about 0.4% to about 4.0%.

Preferably, in view of the desire for a clear product appearance, the surfactant system is substantially soluble in the composition at the level used. By "substantially soluble" surfactant system, what is meant is that the composition has a transmittance of about 25% or more, preferably about 35% or more, more preferably 40% or more, still more preferably about 50% or more, even more preferably about 60% or more at 25° C. when containing the surfactant system at the level used.

The surfactant system useful herein is selected from the group of consisting of a cationic surfactant, a nonionic surfactant, and mixtures thereof.

Cationic Surfactant

Cationic surfactants can be included in the compositions at a level by weight of from about 0.1 to 4.0%, preferably from about 0.2% to about 3.0%, more preferably from about 0.5% to about 1.2%. When quaternary ammonium salt cationic surfactants are contained in the compositions for leave-on use, they can be included at a level of from about 0.05% to about 1.0%, preferably from about 0.1% to about 0.5%.

A variety of cationic surfactants including mono- and di-alkyl chain cationic surfactants can be used in the compositions of the present invention as described below. Among them, preferred are mono-alkyl chain cationic surfactants such as mono-alkyl chain quaternary ammonium salts. The mono-alkyl chain quaternary ammonium salts useful herein are those having mono-long alkyl chain which has from 12 to 20 carbon atoms, preferably from 16 to 18 carbon atoms. Highly preferred mono-alkyl chain quaternary ammonium salts are, for example, cetyl trimethyl ammonium chloride, stearyl trimethyl ammonium chloride. Although the mono-alkyl chain cationic surfactants are preferred, other cationic surfactants such as di-alkyl chain cationic surfactants may also be used alone, or in combination with the mono-alkyl chain cationic surfactants and/or nonionic surfactants. For the compositions for leave-on use, the above preferred cationic surfactants may be used in combination with tertiary amido amines having an alkyl group of from about 12 to about 22 carbons.

Cationic surfactants useful herein include, for example, those corresponding to the general formula (I):

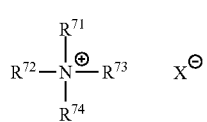

wherein at least one of $R^{71}$, $R^{72}$, $R^{73}$ and $R^{74}$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, the remainder of $R^{71}$, $R^{72}$, $R^{73}$ and $R^{74}$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^{71}$, $R^{72}$, $R^{73}$ and $R^{74}$ are independently selected from $C_1$ to about $C_{22}$ alkyl.

Among the cationic surfactants of general formula (I), preferred are those containing in the molecule at least one alkyl chain having at least 16 carbons. Nonlimiting examples of such preferred cationic surfactants include: behenyl trimethyl ammonium chloride available, for example, with tradename Genamine KDMP from Clariant, with tradename INCROQUAT TMC-80 from Croda, and with tradename ECONOL TM22 from Sanyo Kasei; cetyl trimethyl ammonium chloride available, for example, with tradename CTAC 30KC from KCl, and with tradename CA-2350 from Nikko Chemicals; stearyl trimethyl ammonium chloride available, for example, with tradename Genamine STACP from Clariant; olealkonium chloride available, for example, with tradename Incroquat O-50 from Croda; hydrogenated tallow alkyl trimethyl ammonium chloride, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Also preferred are hydrophilically substituted cationic surfactants in which at least one of the substituents contain one or more aromatic, ether, ester, amido, or amino moieties present as substituents or as linkages in the radical chain, wherein at least one of the $R^{71}$-$R^{74}$ radicals contain one or more hydrophilic moieties selected from alkoxy (preferably $C_1$-$C_3$ alkoxy), polyoxyalkylene (preferably $C_1$-$C_3$ polyoxyalkylene), alkylamido, hydroxyalkyl, alkylester, and combinations thereof. Preferably, the hydrophilically substituted cationic conditioning surfactant contains from 2 to about 10 nonionic hydrophile moieties located within the above stated ranges. Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof; for example, commercially available under the following tradenames; VARISOFT 110, VARISOFT 222, VARIQUAT K1215 and VARIQUAT 638 from Witco Chemical, MACKPRO KLP, MACKPRO WLW, MACKPRO MLP, MACKPRO NSP, MACKPRO NLW, MACKPRO WWP, MACKPRO NLP, MACKPRO SLP from McIntyre, ETHOQUAD 18/25, ETHOQUAD O/12PG, ETHOQUAD C/25, ETHOQUAD S/25, and ETHODUOQUAD from Akzo, DEHYQUAT SP from Henkel, and ATLAS G265 from ICI Americas. Babassuamidopropalkonium Chloride available from Croda under the tradename Incroquat BA-85 is also preferably used in the composition.

Amines are suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethyl amine, palmitamidopropyldimethylamine, palmitamidopropyldiethyl amine, palmitamidoethyldiethylamine, palmitamidoethyldimethyl amine, behenamidopropyldimethylamine, behenamidopropyldiethyl amine, behenamidoethyldiethylamine, behenamidoethyldimethylamine, arachidamidopropyldimethylamine, arachidamidopropyldiethyl amine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Nonionic Surfactant

Nonionic surfactants can be included in the compositions at a level by weight of from about 0.1 to 6.0%, preferably from about 0.4% to about 5.0%, more preferably from about 1.0% to about 4.0%.

A variety of nonionic surfactants can be used in the compositions of the present invention. Among them, preferred nonionic surfactants include, for example, polyethylene glycol derivatives of glycerides, ethylene glycol ethers of fatty alcohols, and polysorbate.

Polyethylene glycol derivatives of glycerides useful herein include derivatives of mono-, di- and tri-glycerides and mixtures thereof. One class of polyethylene glycol derivatives of glycerides suitable herein is those which conform to the general formula (I):

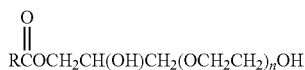

wherein n, the degree of ethoxylation, is from about 4 to about 200, preferably from about 5 to about 150, more preferably from about 20 to about 120, and wherein R comprises an aliphatic radical having from about 5 to about 25 carbon atoms, preferably from about 7 to about 20 carbon atoms. Suitable polyethylene glycol derivatives of glycerides can be polyethylene glycol derivatives of hydrogenated castor oil. Such polyethylene glycol derivatives of hydrogenated castor oil include, for example, PEG-20 hydrogenated castor oil, PEG-30 hydrogenated castor oil, PEG-40 hydrogenated castor oil, PEG-45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil. Other suitable polyethylene glycol derivatives of glycerides can be polyethylene glycol derivatives of stearic acid. Such polyethylene glycol derivatives of stearic acid include, for example, PEG-30 stearate, PEG-40 stearate, PEG-50 stearate, PEG-75 stearate, PEG-90 stearate, PEG-100 stearate, PEG-120 stearate, and PEG-150 stearate.

Ethylene glycol ethers of fatty alcohols useful herein include any ethylene glycol ethers of fatty alcohols which are suitable for use in a hair conditioning composition. No limiting examples of the ethylene glycol ethers of fatty alcohols include; the ceteth series of compounds such as ceteth-1 through ceteth-45, preferably ceteth-7 through ceteth-20; the isoceteth series of compounds such as isoceteth-20; the steareth series of compounds such as steareth-1 through 100; ceteareth 1 through ceteareth-50; the laureth series of compounds, preferably laureth-7 through Laureth-12; the pareth series of compounds, preferably pareth-9 through pareth-15; propylene glycol ethers of the above ceteth, steareth, ceteareth, and laureth series of compounds, such propylene glycol ethers of ceteth series of compounds including, for example, PPG-5-Ceteth-20; polyoxyethylene ethers or polyoxyethylene-polyoxypropylene ethers of branched alcohols, such branched alcohols including, for example, octyldodecyl alcohol, decyltetradecyl alcohol, dodecylpentadecyl alcohol, hexyldecyl alcohol, and isostearyl alcohol, and such polyoxyethylene-polyoxypropylene ethers of branched alcohols including, for example, POE(20)POP(6) decyltetradecyl ether; and mixtures thereof.

Polysorbates useful herein include, for example, polysorbate-20 (POE(20) sorbitan monolaurate) having HLB value of 16.7, polysorbate-21 (POE(4) sorbitan monolaurate) having HLB value of 13.3, polysorbate-40 (POE(20) sorbitan monopalmitate) having HLB value of 15.6, polysorbate-60 (POE(20) sorbitan monostearate) having HLB value of 14.9, polysorbate-61 (POE(4) sorbitan monostearate) having HLB value of 9.6, polysorbate-80 (POE(20)sorbitan monooleate) having HLB value of 15.0, and polysorbate-81 (POE(4) sorbitan monooleate) having HLB value of 10.0.

Preferably, the nonionic surfactants useful herein have an HLB value of from about 8 to about 28, more preferably from about 11 to about 20, still preferably from about 13 to about 15.

Among a variety of nonionic surfactants described above, highly preferred are those selected from the group consisting of isoceteth-20, PPG-5-Ceteth-20, PEG-40 hydrogenated castor oil, polysorbate-20, laureth-20, ceteth-10, ceteth-20, pareth-9, and mixtures thereof.

Hydrophobically Modified Amido Silicone Copolyol

The compositions of the present invention comprise a hydrophobically modified amido silicone copolyol. The inventors have found that hydrophobically modified amido silicone copolyol provides balanced clarity and conditioning benefit. Silicone copolyols which is not hydrophobically modified may have better clarity, however, they do not provide sufficient conditioning benefit. The silicone compound is included in the compositions at levels by weight of from about 0.1% to about 10%, more preferably from about 0.5% to about 8%, still more preferably from about 1% to about 6%, even more preferably from about 1.5% to about 5%.

The hydrophobically modified amido silicone copolyol useful herein are those being substantially soluble in the composition, in view of the desire for clear product appearance. By "substantially soluble" silicone compound, what is meant is that the composition has a transmittance of about 25% or more, preferably about 35% or more, more preferably 40% or more, still more preferably about 50% or more, even more preferably about 60% or more at 25° C. when containing the silicone compound at the level used.

Preferably, in view of clear product appearance, especially avoiding yellowing of the product appearance, the hydrophobically modified amido silicone copolyols are those being substantially free of primary amine groups. The primary amine groups include, for example, reaction residue of amidation. Amido groups are often made from amino groups attached to the silicone backbone, however, some amino groups sometimes remain as reaction residue. What is meant by being "substantially free of primary amine groups" is that the silicone compounds has a Percent primary amine (PPA) of 1% or less, preferably 0.5% or less, more preferably 0% of primary amine groups, wherein PPA is calculated according to the following equation: 100×(number of siloxane groups having primary amine groups)/(number of total siloxane groups).

Highly preferred hydrophobically modified amidomethicone copolyols have the following formula:

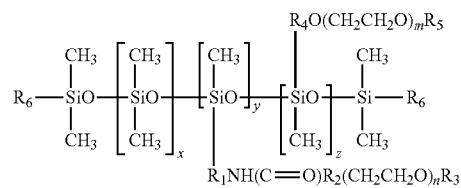

wherein $R_1$, $R_2$, $R_4$ are respectively C1-C3 alkyl, preferably ethyl; $R_3$ is an alkyl group having 8-22 carbon atoms, preferably 10-20 carbon atoms, more preferably 12-16 carbon atoms, even more preferably 12 carbon atoms; $R_5$ is H or C1-C3 alkyl, preferably methyl; $R_6$ is OH or $CH_3$, preferably methyl; n is an integer of 0-10, preferably 1-10, highly preferably 5; m is an integer of 1-30, preferably 2-20, highly preferably 4-16; n+m=2-40, preferably 3-30, more preferably 5-25, still more preferably 8-20, even more preferably 12-18; x, y and z are integers, and defined below in detail. When n is an integer of 0, the substitution containing the amido group has the following formula: $-R_1NH(C=O)R_3$.

In the above formula of highly preferred hydrophobically modified amidomethicone copolyols, it is preferred that: x, y and z are integers of 1 or more; x, y and z are integers such that the above formula has Degree of Polymerization (DP), which corresponds to x+y+z+2, of 100-3200, preferably 200-1000; z is included at a level such that Percent z (Pz) is in the range of from about 2.8% to about 7.0%, preferably from about 3.0% to about 6.5%, wherein the Pz is calculated according to the following equation: Pz=(z/DP)×100; y is included at a level such that Percent y (Py) is in the range of from about 1% to about 15%, preferably from about 2.5% to about 12%, wherein Py is calculated according to the following equation: Py=(y/DP)×100.

Commercially available hydrophobically modified amido silicone copolyols having the above formula are, for example, those having an INCI name PEG-12 Methyl Ether/Lauroxy PEG-5 Amidopropyl Dimethicone.

The above "Percent y" is preferred in view of improved wet conditioning benefits. The above "Percent z" is preferred in view of improved clear product appearance, improved stability of clear product appearance (i.e., improved stability of transmittance and viscosity of the composition) and improved stability of viscosity of the composition. Hydrophobically modified amido silicone copolyols having the same INCI name have a variety of "Percent z". For example, a hydrophobically modified amido silicone copolyol available from Dow Corning with a tradename Silicone BY16-906 has also an INCI name PEG-12 Methyl Ether/Lauroxy PEG-5 Amidopropyl Dimethicone, however, this material has a "Percent z" of about 2.5%. Furthermore, the material available from Dow Corning with a tradename Silicone BY16-906 has a Percent primary amine (PPA) of about 2.5%. The inventors of the present invention have found that this material available from Dow Corning with a tradename Silicone BY16-906 does not meet at least one needs selected from: transmittance of 25% or more; improved stability of clear product appearance; improved stability of viscosity; and avoiding yellowing of the product appearance.

In view of providing improved conditioning benefits, it is preferred for the compositions of the present invention to provide improved silicone deposition, even after rinsing-off the compositions from the hair. For example, it is preferred for the compositions to provide silicone deposition of about 50 ppm or more, more preferably about 100 ppm or more, still more preferably about 150 ppm, even more preferably about 300 ppm or more after rinsing-off the hair. The amount of the silicone deposition can be measured by a method consisting of: (i) a preparation of hair switch; and (ii) silicone deposition measurement.

(i) Preparation of Hair Switch

For the silicone deposition measurement, 2 gram hair switches are used. The hair switches are prepared by following steps:
  (a) Providing five cycles of shampoo/conditioning treatments to the hair switch, each cycle of shampoo/conditioning treatment consisting of following steps:
    (a-1) Applying a shampoo at a level of 0.2 cc and lathering the hair switch; and rinsing the hair switch;
    (a-2) Applying a shampoo again at a level of 0.2 cc and lathering the hair switch; and rinsing the hair switch; and
    (a-3) Then providing conditioner treatment to the hair switch, the conditioner treatment consisting of applying a conditioner at a level of 0.2 cc and treating the hair switch; and rinsing the hair switch; and
  (b) Then drying the hair switch.

The hair switch is ready for the measurement of its silicone deposition amount.

(ii) Silicone Deposition Measurement

The deposited silicone on the hair switch is extracted in an appropriate solvent. The extracts are then introduced into an atomic absorption/emission detector instrument and measured at the appropriate wavelength. The absorbance/emission value returned by the instrument is then converted to actual concentration (ppm) of silicone compound deposited on the hair through an external calibration curve obtained with known weights of a well characterized standard of the silicone compound under study.

Aqueous Carrier

The compositions of the present invention comprise an aqueous carrier. The level and species of the carrier are selected according to the compatibility with other components, and other desired characteristic of the product.

Carriers useful in the present invention include water and water solutions of lower alkyl alcohols. Lower alkyl alcohols useful herein are monohydric alcohols having 1 to 6 carbons, more preferably ethanol and isopropanol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 40% to about 98%, and more preferably from about 50% to about 98% water.

The pH of the present compositions are preferably from about 2 to about 8, more preferably from about 3 to about 7, still more preferably from 4 to 6. Buffers and other pH adjusting agents can be included to achieve the desirable pH.

Cationic Polymer

The conditioning compositions of the present invention preferably include cationic polymers. The cationic polymers hereof will generally have a weight average molecular weight which is at least about 5,000 AMU, typically at least about 10,000 AMU, and is less than about 50 million AMU, typically less than about 10 million AMU, preferably, the molecular weight is from about 100,000 AMU to about 5 million AMU, more preferably from about 500,000 AMU to about 3 million AMU. The cationic polymers useful herein have a cationic charge density of preferably from about 0.05 meq/g to about 4.5 meq/g, more preferably about 0.1 meq/g to about 4.5 meq/g, still more preferably about 0.5 meq/g to about 4.5 meq/g.

The cationic polymer can be included in the compositions at a level by weight of preferably from about 0.05% to about 5%, more preferably from about 0.1% to about 3%, still more preferably from about 0.5% to about 2%. Preferably, in view of the desire for a clear product appearance, the cationic polymer is substantially soluble in the composition at the level used. By "substantially soluble" cationic polymer, what is meant is that the composition has a transmittance of about 25% or more, preferably about 35% or more, more preferably 40% or more, still more preferably about 50% or more, even more preferably about 60% or more at 25° C. when containing the cationic polymer at the level used.

Suitable cationic conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, Polyquaternium-7 including that commercially available with tradenames Merquat 550 and Merquat S from Ondeo Nalco; polymethacrylamidopropyl trimonium chloride such as that commercially available with a tradename Polycare 133 from Rhone-Poulenc; and Polyquaternium-37 available from 3V Sigma with tradenames Synthalen CR, Synthalen CU, and Synthalen CN.

Also suitable cationic conditioning polymers herein include cationic cellulose derivatives. Cationic cellulose derivative useful herein include, for example, salts of hydroxyethyl cellulose reacted with trimethyl ammonium substituted epoxide, referred to in the industry (CTFA) as Polyquaternium 10, available from Amerchol Corp. (Edison, N.J., USA) in their Polymer JR® and KG® series, and also available from National Starch & Chemical with a tradename Celquat SC-230M; and Polyquaternium-4 with tradename Celquat H-100 available from National Starch & Chemical.

Cationic guar polymers, such as guar hydroxypropyltrimonium chloride commercially available from Rhodia in their Jaguar series, can also be used in the present composition. However, in view of product stability in clear product appearance, the compositions of the present invention are preferably substantially free of cationic guar polymers. In the present invention, the composition being "substantially free of cationic guar polymers" means that the composition includes 0.1% or less, preferably 0% of cationic guar polymers.

Other Additional Components

The compositions of the present invention may include additional components, which may be selected by the artisan according to the desired characteristics of the final product and which are suitable for rendering the compositions more cosmetically or aesthetically acceptable or to provide them with additional usage benefits.

Humectant and/or Co-Solvent

The compositions of the present invention may contain a humectant and/or co-solvent to help the surfactant system and/or silicone compound to be substantially soluble in the composition. The humectants and/or co-solvents herein are selected from the group consisting of polyhydric alcohols, water soluble alkoxylated nonionic polymers, water soluble alkyl alcohols and mixtures thereof. The humectants and/or co-solvents herein are preferably used at levels by weight of the compositions of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sultate, sodium hyaluronate, sodium adenosin phosphate, sodium lactate, pyrrolidone carbonate, glucosamine, cyclodextrin, and mixtures thereof. Among them, preferred for the co-solvents are 1,2-hexane diol, hexylene glycol, butylene glycol, glycerine, and mixtures thereof.

Water soluble alkyl alcohols useful herein include, for example, monohydric C1-6 alkyl alcohols such as ethanol, isopropyl alcohol, propanol, and benzyl alcohol.

Water soluble alkoxylated nonionic polymers useful herein include polyethylene glycols and polypropylene glycols having a molecular weight of up to about 10,000 AMU such as those with CTFA names PEG-4, PEG-8, PEG-12, PEG-20, PEG-150 and mixtures thereof.

Other Additional Components

The compositions of the present invention may further include other additional components. Other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, nonionic surfactants such as glyceryl stearate available from Stepan Chemicals, hydrolysed keratin, proteins, plant extracts, and nutrients; emollients such as PPG-3 myristyl ether with tradename Varonic APM available from Goldschmidt, Trimethyl pentanol hydroxyethyl ether, PPG-11 stearyl ether with tradename Varonic APS available from Goldschmidt, Stearyl heptanoate with tradename Tegosoft SH available from Goldschmidt, Lactil (mixture of Sodium lactate, Sodium PCA, Glycine, Fructose, Urea, Niacinamide, Inositol, Sodium Benzoate, and Lactic acid) available from Goldschmidt, Ethyl hexyl palmitate with tradename Saracos available from Nishin Seiyu and with tradename Tegosoft OP available from Goldschmidt; hair-fixative polymers such as amphoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; and sequestering agents, such as disodium ethylenediamine tetra-acetate; ultraviolet and infrared screening and absorbing agents such as octyl salicylate; antidandruff agents such as zinc pyrrithione and salicylic acid; visible particles with tradenames Unisphere and Unicerin available from Induchem AG (Switzerland); and anti-foaming agent such as that with a tradename XS63-B8929 available from GE-Toshiba Silicone.

When the compositions are for leave-on use, it is preferred to use the combination of the following preservatives: disodium EDTA, methyl paraben, propyl paraben, benzyl alcohol, and phenoxyethanol.

Product Forms

The conditioning compositions of the present invention can be in the form of rinse-off products or leave-on products, and can be formulated in a wide variety of product forms, including but not limited to creams, gels, emulsions, mousses and sprays.

The conditioning compositions of the present invention can be used for conditioning a hair and/or skin, by applying the compositions to hair and/or skin. The conditioning compositions of the present invention are especially suitable for hair care products such as hair conditioners and skin care products such as skin conditioners.

The conditioning compositions of the present invention are especially suitable for hair conditioners for rinse-off or leave-on use. When the conditioning compositions are for rinse-off use, such compositions are preferably used by following steps:
(i) after shampooing hair, applying to the hair an effective amount of the conditioning compositions for conditioning the hair; and
(ii) then rinsing the hair.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

| Compositions (wt %) | Ex.1 | Ex.2 | Ex.3 | Ex.4 | Ex.5 | Ex.6 | Ex.7 |
|---|---|---|---|---|---|---|---|
| Nonionic thickening polymer-1 *1 | 1.4 | 1.2 | — | — | — | — | — |
| Nonionic thickening polymer-2 *2 | — | — | 0.5 | 2.0 | 1.2 | 0.5 | 1.2 |
| Cationic conditioning polymer-1 *3 | 0.7 | — | 1.5 | — | 0.7 | 1.5 | — |
| Cationic conditioning polymer-2 *4 | — | 0.7 | — | 0.5 | — | — | 0.5 |
| Cationic conditioning polymer-3 *5 | — | — | — | — | — | — | 0.5 |
| Cetyltrimethylammonium chloride | 1.0 | 1.0 | 1.0 | 1.0 | 1.0 | 1.0 | 1.0 |
| Stearyltrimethylamonium Chloride | — | — | — | — | — | 0.25 | — |
| C12-14 Pareth-9 *6 | — | — | 3.0 | — | — | 3.0 | — |
| Hydrophobically modified amido silicone copolyol-1 *7 | 2.0 | — | — | — | — | 2.0 | — |
| Hydrophobically modified amido silicone copolyol-2 *8 | — | 2.0 | — | 0.5 | 2.0 | — | 2.0 |
| Hydrophobically modified amido silicone copolyol-3 *9 | — | — | 8.0 | — | — | 2.0 | — |
| Methylchloroisothiazolinone/Methylisothiazolinone *10 | 0.025 | 0.025 | 0.025 | 0.025 | 0.025 | 0.025 | 0.025 |
| Methyl Paraben | 0.2 | 0.2 | 0.2 | 0.2 | 0.2 | 0.2 | 0.2 |
| Disodium EDTA | 0.1 | 0.1 | 0.1 | 0.1 | 0.1 | 0.1 | 0.1 |
| Perfume | 0.6 | 0.7 | — | 0.3 | 0.7 | 0.1 | 0.5 |
| Deionized Water | q.s. to 100% | | | | | | |

| | Ex.8 | Ex.9 | Ex.10 | Ex.11 | Ex.12 | Ex.13 | Ex.14 |
|---|---|---|---|---|---|---|---|
| Nonionic thickening polymer-1 *1 | 0.5 | 0.5 | 1.0 | 2.0 | 1.2 | 1.4 | 1.2 |
| Cationic conditioning polymer-1 *3 | — | 0.5 | — | — | — | — | 0.7 |
| Cationic conditioning polymer-2 *4 | — | — | — | 0.5 | — | 0.7 | — |
| Cationic conditioning polymer-3 *5 | 1.0 | 0.5 | — | — | 0.7 | — | — |
| Cetyltrimethylammonium chloride | 1.4 | 0.5 | 1.0 | 0.6 | 1.0 | 1.0 | 1.0 |
| C12-14 Pareth-9 *6 | 3.0 | — | 0.5 | 1.0 | — | — | — |
| Hydrophobically modified amido silicone copolyol-1 *7 | 8.0 | — | 2.0 | — | — | — | — |
| Hydrophobically modified amido silicone copolyol-2 *8 | — | 1.5 | 2.0 | 0.5 | 2.0 | 2.0 | 2.0 |
| Methylchloroisothiazolinone/Methylisothiazolinone *10 | 0.025 | 0.025 | 0.025 | 0.025 | 0.025 | 0.025 | 0.025 |
| Methyl Paraben | 0.2 | 0.2 | 0.2 | 0.2 | 0.2 | 0.2 | 0.2 |
| Disodium EDTA | 0.1 | 0.1 | 0.1 | 0.1 | 0.1 | 0.1 | 0.1 |
| Perfume | 0.1 | 0.3 | 0.1 | 0.3 | 0.6 | 0.7 | 0.7 |
| Dye | 0.0003 | 0.0003 | 0.0003 | 0.0003 | 0.0003 | 0.0003 | 0.0003 |
| Deionized Water | q.s. to 100% | | | | | | |

| | Ex.15 | Ex.16 | Ex.17 | Ex.18 | Ex.19 | Ex.20 | Ex.21 |
|---|---|---|---|---|---|---|---|
| Nonionic thickening polymer-1 *1 | 1.0 | 0.5 | — | — | 1.3 | — | 0.5 |
| Nonionic thickening polymer-2 *2 | — | — | 2.0 | 1.5 | — | 1.0 | — |
| Cationic conditioning polymer-1 *3 | — | — | 0.2 | — | — | 0.7 | 0.3 |
| Cationic conditioning polymer-2 *4 | 1.0 | — | — | — | 0.5 | — | 1.5 |
| Cationic conditioning polymer-3 *5 | — | 1.5 | — | 0.2 | — | — | — |
| Cetyltrimethylammonium chloride | 0.5 | 0.2 | 0.3 | 0.1 | 0.1 | — | 0.1 |
| Stearyltrimethylammonium Chloride | — | — | — | 0.2 | 0.4 | 0.5 | 0.4 |
| Stearamidopropyldimethylamine | — | — | — | 0.5 | 1.0 | 0.7 | 1.0 |
| C12-14 Pareth-9 *6 | — | — | — | — | — | 0.5 | 0.7 |
| Hydrophobically modified amido silicone copolyol-1 *7 | — | — | 1.0 | — | — | 1.0 | — |
| Hydrophobically modified amido silicone copolyol-2 *8 | 1.0 | 0.5 | — | — | 0.5 | — | 1.0 |
| Hydrophobically modified amido silicone copolyol-3 *9 | — | — | — | 1.0 | — | — | — |
| Citric acid | — | — | — | 0.1 | 0.2 | 0.1 | 0.2 |
| Disodium EDTA | 0.1 | 0.1 | 0.1 | 0.1 | 0.1 | 0.1 | 0.1 |

-continued

| Compositions (wt %) | | | | | | | |
|---|---|---|---|---|---|---|---|
| Methyl Paraben | 0.2 | 0.2 | 0.2 | 0.2 | 0.2 | 0.2 | 0.2 |
| Propyl Paraben | 0.1 | 0.1 | 0.1 | 0.1 | 0.1 | 0.1 | 0.1 |
| Benzyl alcohol | 0.4 | 0.4 | 0.4 | 0.4 | 0.4 | 0.4 | 0.4 |
| Pheoxyethanol | 0.4 | 0.4 | 0.4 | 0.4 | 0.4 | 0.4 | 0.4 |
| Perfume | 0.3 | 0.5 | 0.7 | 0.3 | 0.5 | 0.2 | 0.3 |
| De-ionized water | | | | q.s. to 100% | | | |

Definitions of Components
*1 Nonionic thickening polymer-1: Jaguar HP-105 having a molecular weight of about 2,000,000 AMU available from Rhodia
*2 Nonionic thickening polymer-2: Hydroxyethyl Ethylcellulose having a tradename Elfacos CD 481 available from AKZONOBEL
*3 Cationic conditioning polymer-1: Polyquaternium-10 having a tradename Polymer JR30M available from Amerchol
*4 Cationic conditioning polymer-2: Polyquaternium-4 having a tradename Celquat H100 available from National Starch
*5 Cationic conditioning polymer-3: Jaguar Excel available from Rhodia
*6 C12-14 Pareth-9: BT-9 available from Nikkol
*7 Hydrophobic ally modified amido silicone copolyol-1: Hydrophobically modified amidomethicone copolyol having the following formula (i):

(i)

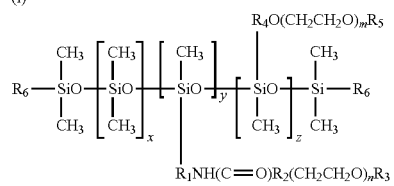

wherein $R_1$, $R_2$, $R_4$ are ethyl; $R_3$ is an alkyl group having 12 carbon atoms; $R_5$ and $R_6$ are methyl; n is an integer of 5; m is an integer of 12; x, y and z are integers of 1 or more; the formula has DP (x + y + z + 2) of about 280, Pz of about 3.5% and Py of about 5.7%.
*8 Hydrophobically modified amido silicone copolyol-2: Hydrophobically modified amidomethicone copolyol having the above formula (i), but having different Pz (Pz of about 3.6%) and Py (Py of about 2.9%) values.
*9 Hydrophobically modified amido silicone copolyol-3: Hydrophobically modified amidomethicone copolyol having the above formula (i), but having different DP value, DP = 750
*10 Methylchloroisothiazolinone/Methylisothiazolinone: Kathon CG available from Rohm&Haas Method of Preparation The conditioning compositions of "Ex.1" to "Ex.14" as shown above can be prepared by any conventional method well known in the art. They are suitably made as follows:

The polymeric materials are dispersed in water at room temperature, mixed with vigorous agitation, and heated to 50-70° C. Cationic surfactants, and if included, nonionic surfactants, humectants, and other temperature insensitive components are added to the mixture with agitation. Then the mixture is cooled down to below 40° C., and then the remaining components such as silicones, perfumes, preservatives, and anti-foaming agents, if included, are added to the mixture with agitation.

Examples 1 through 14 are conditioning compositions of the present invention which are particularly useful for hair conditioners for rinse-off use. Examples 15 through 21 are conditioning compositions of the present invention which are particularly useful for hair conditioners for leave-on use. The compositions of "Ex.1" through "Ex.21" have a viscosity of from about 1,000 cps to 50,000 cps and Shear Thinning Index of 30 or more. The compositions of "Ex.1" through "Ex.21" have a transmittance of 25% or more. These examples have many advantages. For example, the compositions of "Ex.1" through "Ex.21" have a clear product appearance and a suitable rheology for conditioning compositions. The compositions of "Ex.1" through "Ex.21" have such transmittance and rheology for at least one month at 25° C. following preparation of the composition. The compositions of "Ex.1" through "Ex.21" can provide conditioning benefits, especially softness and reduced tangling when used for hair care products such as hair conditioning products. When used for hair care products, the compositions of "Ex.1" through "Ex.21" can provide the above benefits while not weighing down the hair.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair or skin conditioning composition comprising by weight:
   (a) from about 0.1% to about 10% of a thickening polymer system;
   (b) from about 0.1% to about 8.0% of a surfactant system selected from the group consisting of cationic surfactant, nonionic surfactant, and mixtures thereof;
   (c) from about 0.1% to about 10% of a hydrophobically modified amido silicone copolyol having the following formula:

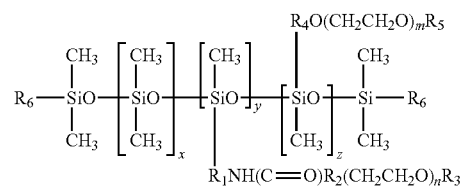

wherein $R_1$, $R_2$, $R_4$ are respectively C1-C3 alkyl; $R_3$ is an alkyl group having 8-22 carbon atoms; $R_5$ is H or C1-C3 alkyl; $R_6$ is OH or $CH_3$; n is an integer of 0-10; m is an integer of 1-30; n+m=2-40; x, y and z are integers 1 or more; the above formula has Degree of Polymerization (DP), which corresponds to x+y+z+2, of 100-3200; z is included at a level such that Percent z (Pz) is in the range of from 2.8% to 7.0%, wherein the Pz is calculated according to the following equation: Pz=(z/DP)×100; y is included at a level such that Percent y (Py) is in the range of from about 1% to about 15%, wherein Py is calculated according to the following equation: Py=(y/DP)×100;
and
(d) an aqueous carrier;
wherein the composition has a transmittance of 25% or more for at least one month at 25° C. following preparation of the composition; and wherein the composition has a viscosity of from about 1,000 cps to about 50,000 cps and Shear Thinning Index of 30 or more for at least for at least one month at 25° C. following preparation of the composition.

2. The conditioning composition of claim 1 wherein the composition has a transmittance of 35% or more.

3. The conditioning composition of claim 2 wherein the composition has a transmittance of 35% or more for at least one month at 25° C. following preparation of the composition.

4. The conditioning composition of claim 1 wherein the composition is substantially free of substantially insoluble oily compounds.

5. The conditioning composition of claim 1 wherein the composition is substantially free of a compound having a primary amine group.

6. The conditioning composition of claim 1 wherein the thickening system is nonionic.

7. The conditioning composition of claim 1 wherein the thickening system comprises a nonionic guar polymer.

8. The conditioning composition of claim 7 wherein the nonionic guar polymer has a molecular weight of from about 500,000 Atomic Mass Units to about 4,000,000 Atomic Mass Units.

9. The conditioning composition of claim 1 wherein the surfactant system is substantially soluble in the composition.

10. The conditioning composition of claim 1 wherein the cationic surfactant is selected from the group consisting of mono-alkyl quaternary ammonium salts, di-alkyl quaternary ammonium salts, hydrophilically substituted mono-alkyl quaternary ammonium salts, hydrophilically substituted di-alkyl quaternary ammonium salts, mono-alkyl chain amines, di-alkyl chain amines, and mixtures thereof.

11. The conditioning composition of claim 1 wherein the cationic surfactant is selected from the group consisting of cetyl trimethyl ammonium chloride, stearyl trimethyl ammonium chloride, di-cetyl dimethyl ammonium chloride, and mixtures thereof.

12. The conditioning composition of claim 1 wherein the nonionic surfactant has an HLB value of from about 8 to about 28.

13. The conditioning composition of claim 12, wherein the nonionic surfactant is selected from the group consisting of isoceteth-20, PPG-5-Ceteth-20, PEG-40 hydrogenated castor oil, polysorbate-20, laureth-20, ceteth-10, ceteth-20, pareth-9, and mixtures thereof.

14. The conditioning composition of claim 1 wherein the hydrophobically modified amido silicone copolyol are those substantially free of primary amine groups.

15. The conditioning composition of claim 1 wherein the Pz is in the range of from about 3% to about 6.5%.

16. The conditioning composition of claim 1 further comprising from about 0.05% to about 5.0% of a cationic polymer.

17. The conditioning composition of claim 1 wherein the composition is substantially free of cationic guar polymers.

18. The conditioning composition of claim 1 comprising by weight:
(a) from about 0.5% to about 5.0% of the thickening polymer system;
(b) from about 0.2% to about 5.0% of the surfactant system;
(c) from about 0.5% to about 8.0% of the hydrophobically modified amido silicone copolyol having the following formula:

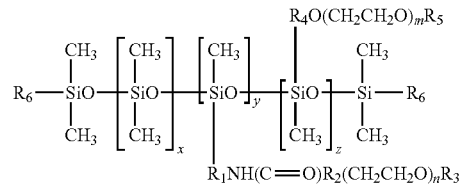

wherein $R_1$, $R_2$, $R_4$ are respectively C1-C3 alkyl; $R_3$ is an alkyl group having 8-22 carbon atoms; $R_5$ is H or C1-C3 alkyl; $R_6$ is OH or $CH_3$; n is an integer of 0-10; m is an integer of 1-30; n+m=2-40; x, y and z are integers 1 or more; the above formula has Degree of Polymerization (DP), which corresponds to x+y+z+2, of 100-3200; z is included at a level such that Percent z (Pz) is in the range of from 2.8% to 7.0%, wherein the Pz is calculated according to the following equation: Pz=(z/DP)×100; y is included at a level such that Percent y (Py) is in the range of from about 1% to about 15%, wherein Py is calculated according to the following equation: Py=(y/DP)×100;
(d) an aqueous carrier; and
(e) from about 0.1% to about 3.0% of a cationic conditioning polymer;
wherein the composition has a transmittance of 25% or more for at least one month at 25° C. following preparation of the composition; and wherein the composition has a viscosity of from about 1,000 cps to about 50,000 cps and Shear Thinning Index of 30 or more for at least for at least one month at 25° C. following preparation of the composition.

19. The conditioning composition of claim 18 comprising by weight:
(a) from about 0.75% to about 4.0% of the thickening polymer system;
(b) from about 0.4% to about 4.0% of the surfactant system;
(c) from about 1.0% to about 6.0% of the hydrophobically modified amido silicone copolyol wherein Pz is in the range of from about 3.0% to about 6.5%;
(d) an aqueous carrier; and
(e) from about 0.1% to about 3.0% of the cationic conditioning polymer;
wherein the composition is substantially free of substantially insoluble oily compounds;
wherein the composition is substantially free of a compound having a primary amine group;
wherein the composition has a transmittance of 25% or more for at least one month at 25° C. following preparation of the composition; and wherein the composition has a viscosity of from about 1,000 cps to about 50,000 cps and Shear Thinning Index of 30 or more for at least for at least one month at 25° C. following preparation of the composition.

20. The conditioning composition of claim 1 which is a hair conditioning composition.

* * * * *